(12) United States Patent
Wahl et al.

(10) Patent No.: US 6,487,899 B1
(45) Date of Patent: Dec. 3, 2002

(54) COMBUSTION DIAGNOSIS SYSTEM (75) Inventors: Claus Wahl, Vaihingen/Enz; Juergen Steinwandel, Uhldingen-Muehlhofen, both of (DE)

(73) Assignee: Deutsches Zentrum fuer Luft -und Raumfahrt e.V., Cologne (DE)

( * ) Notice: Subject to any disclaimer, the term of this patent is extended or adjusted under 35 U.S.C. 154(b) by 0 days.

(21) Appl. No.: 09/483,773

(22) Filed: Jan. 18, 2000

(30) Foreign Application Priority Data

Jan. 19, 1999 (DE) .......................................... 199 01 795

(51) Int. Cl.$^7$ ................................................ G01L 3/26
(52) U.S. Cl. ...................................................... 73/117.3
(58) Field of Search ............................... 73/116, 117.3; 250/554

(56) References Cited

U.S. PATENT DOCUMENTS 4,709,155 A * 11/1987 Yamaguchi et al. ......... 250/554
5,384,467 A * 1/1995 Plimon et al. ............... 250/554

FOREIGN PATENT DOCUMENTS

| DE | 30 39 879 | 6/1982 | | |
|---|---|---|---|---|
| EP | 0 282 295 | 9/1988 | | |
| EP | 0 593 413 | 4/1994 | | |
| GB | 0282295 | * 3/1987 | ........... | F02D/35/02 |
| GB | 2 194 634 | 3/1988 | | |
| GB | 2226659 | * 12/1988 | ........... | F02D/41/14 |
| GB | 2 226 659 | 7/1990 | | |

* cited by examiner

Primary Examiner—Benjamin R. Fuller
Assistant Examiner—Maurice Stevens
(74) Attorney, Agent, or Firm—Barry R. Lipsitz; Douglas M. McAllister (57) ABSTRACT

A diagnostic system for a combustion chamber is provided which comprises a diagnostic element which can be inserted into a wall of the combustion chamber. A plurality of light guides penetrates the diagnostic element for detecting electromagnetic radiation occurring in the combustion chamber. A plurality of detection units is also provided, each detection unit being associated with a corresponding light guide. Each light guide guides the electromagnetic radiation from a spatial segment of the combustion chamber associated with that light guide. The spatial segments are different respective segments of the combustion chamber which are arranged so as not to overlap. Each detection unit detects the electromagnetic radiation from a corresponding light guide for combustion analysis.

15 Claims, 9 Drawing Sheets

COMBUSTION DIAGNOSIS SYSTEM

The invention relates to a combustion diagnosis system for a combustion chamber of a combustion system, comprising a diagnostic element which can be inserted into a combustion chamber wall, communicates with the combustion chamber and is penetrated by a light guide, by means of which electromagnetic radiation occurring in the combustion chamber can be detected.

BACKGROUND OF THE INVENTION

Such a combustion diagnosis system is known from the state of the art. With this combustion diagnosis system, a light guide is guided centrally through an ignition plug in order to detect electromagnetic radiation in the combustion chamber.

It has, however, been shown that the electromagnetic radiation detected does not provide a complete picture of the combustion occurring in the combustion chamber.

SUMMARY OF THE INVENTION

The object underlying the invention is therefore to improve a combustion diagnosis system of the generic type in such a manner that the course of combustion in the combustion chamber can be detected even better.

This object is accomplished in accordance with the invention, in a combustion diagnosis system of the type described at the outset, in that the diagnostic element is penetrated by several light guides and that with each of the several light guides the electromagnetic radiation from a spatial segment of the combustion chamber associated with this light guide is detectable and that the spatial segments are different respective segments of the combustion chamber.

The advantage of the inventive solution is to be seen in the fact that as a result it is possible, due to the use of a plurality of light guides and due to the allocation of different spatial segments to the individual light guides, to analyze the combustion occurring in the combustion chamber in spatial resolution and thus to detect the propagation of the combustion in the combustion chamber considerably better. The spatial propagation of combustion in the combustion chamber may, for example, be analyzed advantageously as a result.

In principle, it would be conceivable to dimension and arrange the spatial segments such that these overlap one another so that the electromagnetic radiation detected in the individual light guides could originate, at least partially, from the same combustion process.

However, in order to obtain a clear, spatial resolution it is preferably provided for the spatial segments of the combustion chamber to be arranged therein so as not to overlap, i.e. the electromagnetic radiation from one spatial segment is detected only by one light guide and the other light guides cannot detect this electromagnetic radiation.

The position of the spatial segments may, in principle, be selected in any optional manner. It is particularly favorable when the spatial segments of the combustion chamber are arranged around a central axis so that the development of the combustion around this central axis can be analyzed advantageously in spatial resolution.

A particularly favorable solution provides for the central axis to represent a central axis of the diagnostic element so that the spatial segments are in a position to cover areas of the combustion chamber located around this central axis.

In the case of an ignition plug designed as diagnostic element, it is preferably provided for the ignition spark generated by this to be located close to the central axis, preferably approximately concentric to it, so that the combustion originating from the ignition spark can be analyzed advantageously.

In addition, in the case of an injection nozzle designed as diagnostic element it is preferably provided for the injection channel to be located close to the central axis, preferably approximately concentric to this, so that the combustion forming around the injected fuel can likewise be analyzed advantageously due to the individual spatial segments.

In this respect, it is particularly favorable when the spatial segments are arranged symmetrically around the central axis so that with the sum of the spatial segments it is possible to analyze a considerable area of the combustion chamber around the central axis in spatial resolution.

It is particularly favorable when the sum of all the spatial segments covers a subsection of the combustion chamber extending around the central axis to a considerable proportion so that it is possible to follow the propagation of the combustion and the resulting electromagnetic radiation connected thereto in the direction of all the radial directions relative to the central axis in spatial resolution.

With respect to the arrangement of the light guides themselves, no further details have so far been given.

One advantageous embodiment, for example, provides for the light guides to be arranged in a passage in a member of the diagnostic element.

It is particularly favorable when one light-guide end of the light guides is located in the passage in front of an opening thereof facing the combustion chamber. The advantage of this solution is to be seen in the fact that with it the light-guide end is arranged so as to be protected in the passage in relation to the combustion chamber.

In this respect it is particularly advantageous when a section of the passage located between the light-guide end and the opening of the passage facing the combustion chamber forms an aperture stop for the electromagnetic radiation entering the light guide.

In order to obtain as large an aperture as possible, it is preferably provided for the cross section of this section to be designed to broaden from the light-guide end as far as the opening of the passage facing the combustion chamber.

In principle, it is conceivable within the scope of the inventive solution to provide the diagnostic element as a separate element, wherein in this case the combustion chamber wall must have an opening for the insertion of the diagnostic element. In this respect, the diagnostic element can preferably be fixed detachably on the combustion chamber wall, for example, be screwed into a threaded opening of the combustion chamber wall.

However, a particularly favorable solution provides for a functionally necessary element of the combustion system to be designed as diagnostic element, i.e. for an element necessary in any case for the functioning of the combustion system, such as, for example, an ignition plug or a spark plug or an injection nozzle, to be designed in addition as diagnostic element.

With respect to the evaluation of the electromagnetic radiations coming from the individual spatial segments, no further details have so far been given. One advantageous embodiment provides for the light guides to be connected to a diagnosis generating unit, preferably guided to it.

Such a diagnosis generating unit could be designed, for example, such that it detects and evaluates the electromagnetic radiation in the individual light guides serially.

It is, however, particularly favorable when each light guide is guided to its own detection unit, wherein this solution is advantageous on account of its constructional simplicity which makes it unnecessary to connect a single detection unit to each individual light guide.

In addition, a further development of this solution is advantageous to the effect that it is possible to detect the electromagnetic radiation in all the light guides simultaneously by means of respective detection units.

The inventive diagnostic system is particularly advantageous when the detection unit detects the electromagnetic radiation in spectral resolution so that it is possible to detect the intensity of individual spectral components.

In this respect, it would be conceivable, in principle, to detect one spectral component with regard to its intensity for each detection unit. Since, however, absolute measurements of the intensity are difficult to evaluate to obtain results concerning an optimum combustion it is preferably provided for the detection unit to detect several spectral components of the electromagnetic radiation so that it is possible to put the intensity of the individual spectral components in relation to one another.

With respect to the evaluation of the intensities detected by the detection units, it is preferably provided for all the detection units to be coupled to a common evaluation unit which then detects the intensities in the individual detection units and puts these in relation to one another on account of the spatial resolution in order to provide a diagnosis of the combustion taking place in the combustion chamber.

In order to detect the combustion processes as extensively as possible it is preferably provided for the diagnostic element to be provided, in addition, with a pressure sensor detecting the pressure in the combustion chamber. Such a pressure sensor enables the state of the combustion to be detected in addition and thus the electromagnetic radiation to be placed in relation to the state of the combustion and evaluated.

A further, advantageous solution provides for the evaluation unit to be coupled to the pressure sensor in order to place the measured pressure in relation to the spatial resolution of the electromagnetic radiation.

Furthermore, it is preferably provided for the evaluation unit to detect, in addition, a mechanical state of the combustion system, in the case of a piston engine the mechanical position of the piston, via a separate sensor.

Additional features and advantages of the inventive solution are the subject matter of the following description as well as the drawings illustrating several embodiments.

DESCRIPTION OF THE PREFERRED EMBODIMENTS

Figure 1:
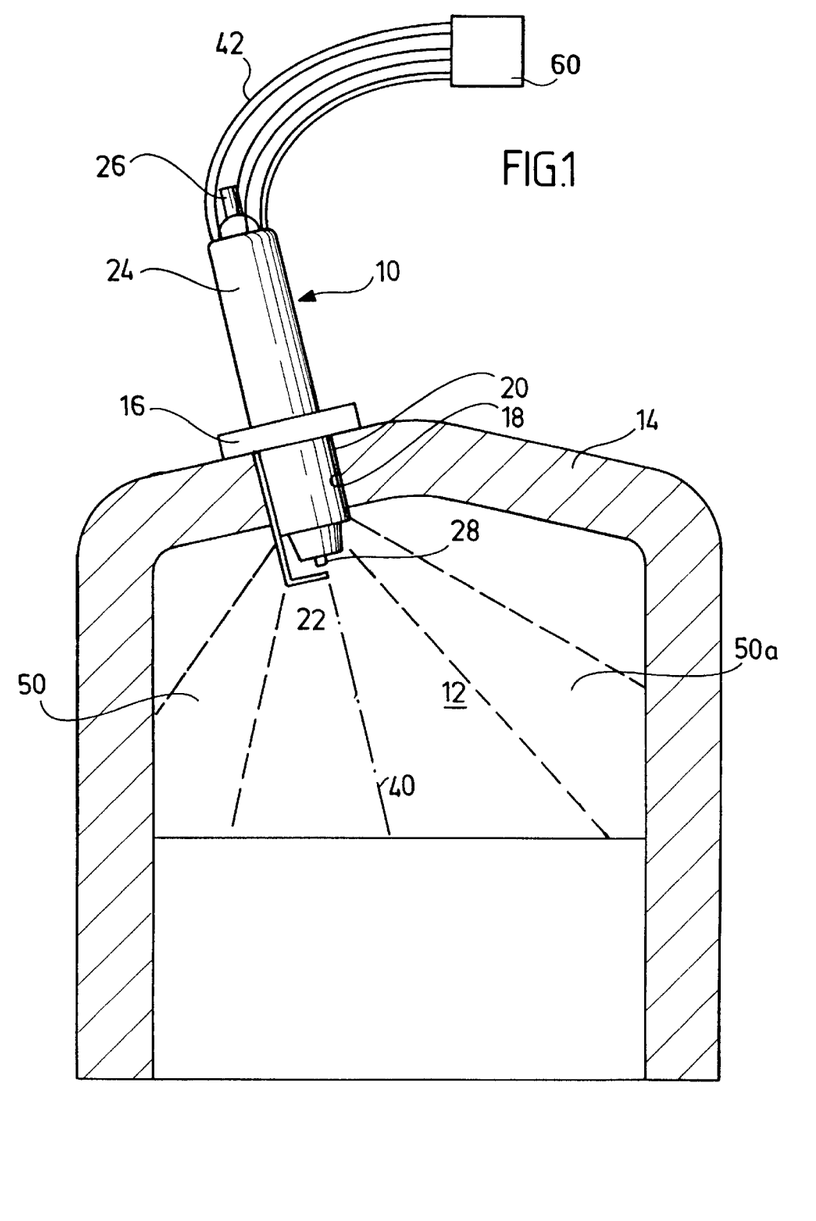
FIG. 1 shows a schematic illustration of a first embodiment of an inventive diagnostic system.

One embodiment of an inventive combustion diagnosis system, illustrated in FIG. 1, comprises a diagnostic element which is designated as a whole as 10 and can be inserted into a combustion chamber wall 14 surrounding a combustion chamber 12 in order to detect electromagnetic radiation occurring in the combustion chamber 12.

The diagnostic element 10 is designed, for example, as an ignition plug and comprises the customary ignition plug elements and functions, i.e., for example, a screw-in member 16 which can be screwed into a threaded bore 18 of the combustion chamber wall 14 with an external thread 20 and bears on its side facing the combustion chamber 10 an earth electrode 22 bent in the customary manner. A ceramic member 24 is inserted into the screw-in member 16 and this insulates a high-voltage electrode 26 passing through the ceramic member in relation to the screw-in member 16 so that the high-voltage electrode 26 projects beyond the ceramic member 24 with a front end 28 and is seated at a defined distance from the earth electrode 22 in order to generate the customary ignition spark.

Figure 2:
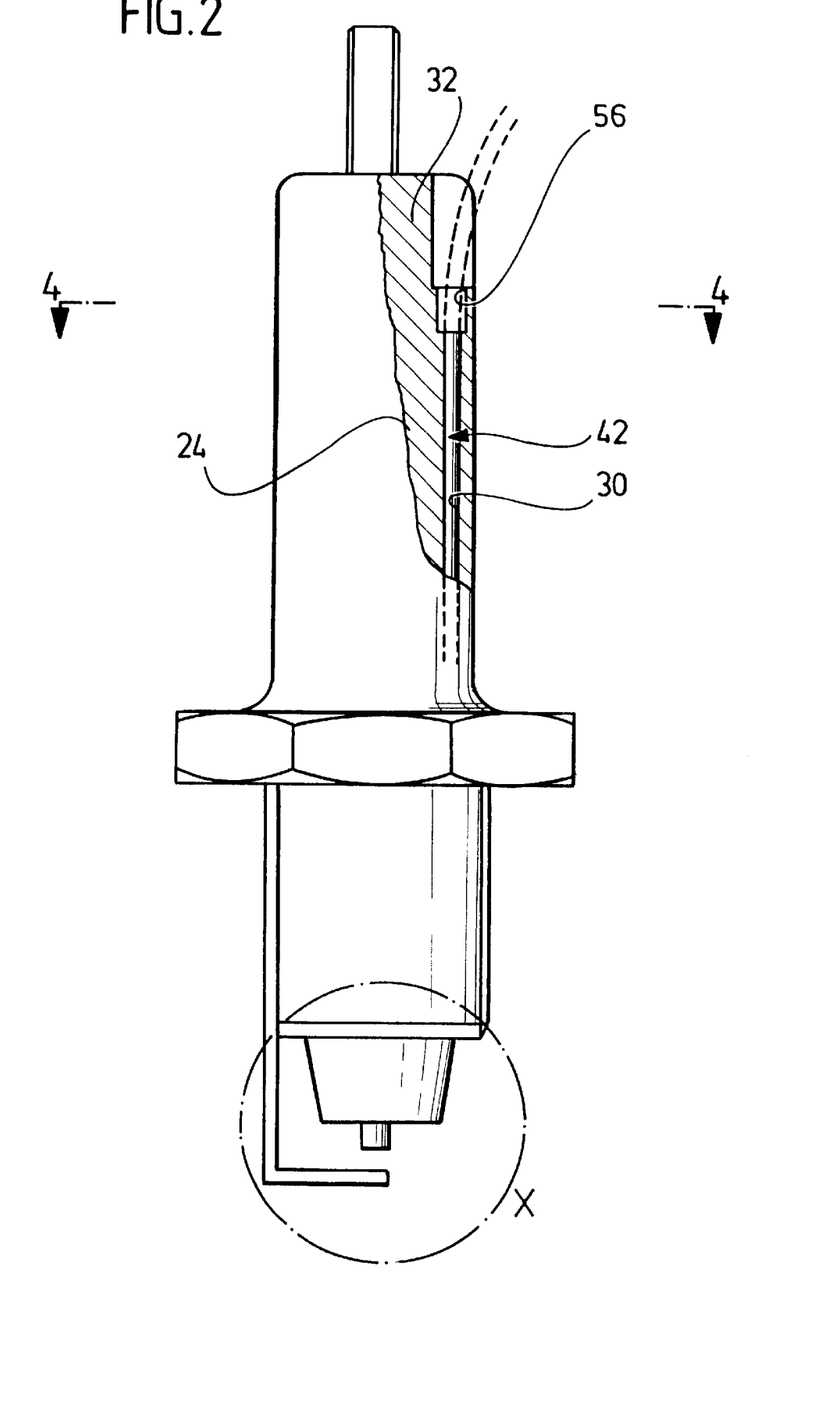
FIG. 2 shows a schematic, partially cutaway illustration of the first embodiment of the diagnostic element.
Figure 3:
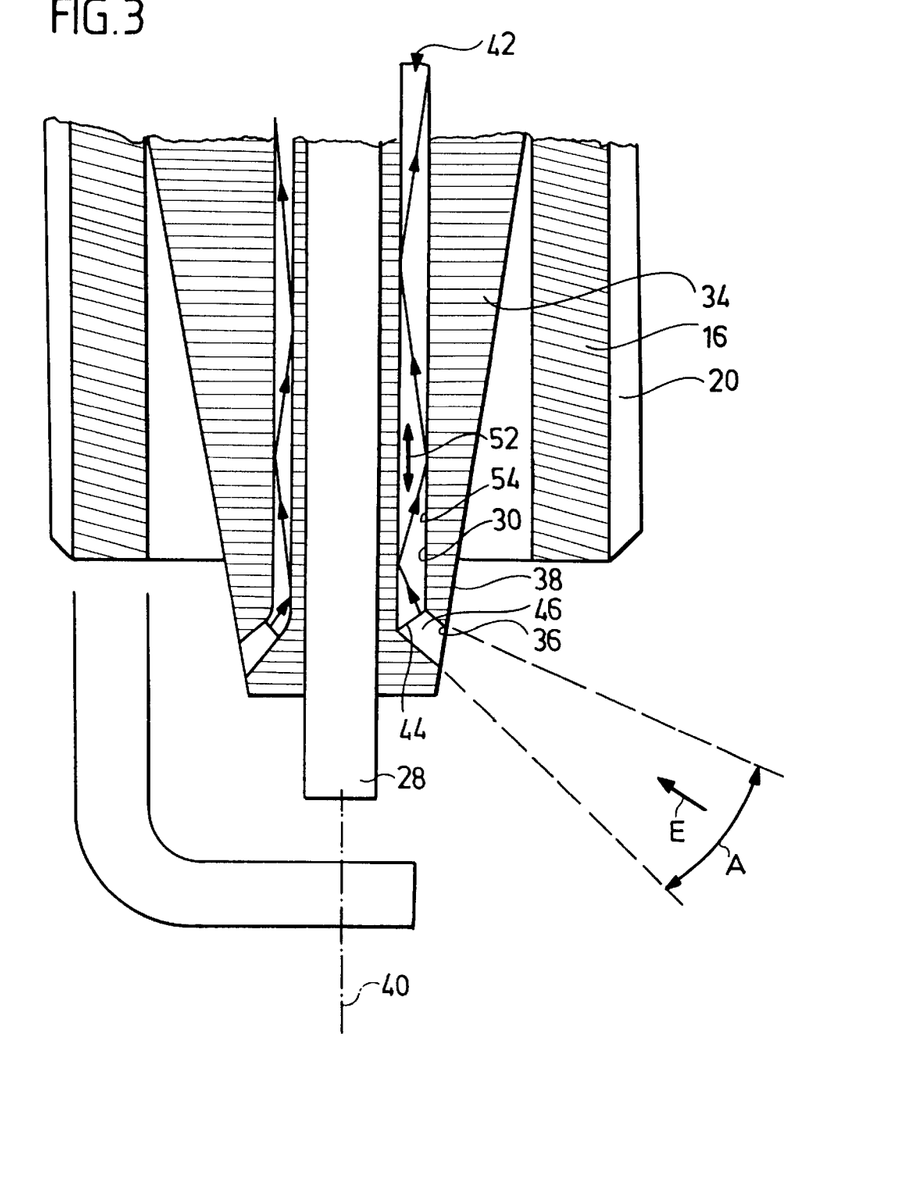
FIG. 3 shows a detail of an enlarged, central section through the area X in FIG. 2.

In addition, the ceramic member 24 is, as illustrated in FIGS. 2 and 3, provided with a plurality of passages 30 which extend through the ceramic member from an end area 32 of the ceramic member facing away from the screw-in member 16 as far as a front end area 34 of the ceramic member 24 tapering conically in relation to the screw-in member 16 and projecting into the combustion chamber 12, as far as an opening 36 on the side of the combustion chamber which is preferably located close to the end 28 of the high-voltage electrode on the side of the combustion chamber and in the area of a conical surface 38 of the front end area 34, wherein the conical surface 38 preferably extends conically to an axis 40 which represents at the same time the central axis of the high-voltage electrode 26.

A light guide designated as a whole as 42 is inserted into each of the passages 30 and this passes through the respective passage 30 and ends with a light-guide end 44 on the side of the combustion chamber which is preferably arranged such that it is still located in the passage 30 passing through the ceramic member 24 at a distance from the opening 36 of the passage on the side of the combustion chamber so that a section 46 of the passage 30 remains between the light-guide end 44 on the side of the combustion chamber and the opening 36 on the side of the combustion chamber, this section serving to protect the light-guide end on the side of the combustion chamber.

The section 46 also serves at the same time, however, to define an aperture stop for the electromagnetic radiation entering from the combustion chamber 12, this stop determining an aperture A, with which a detection of electromagnetic radiation from a spatial segment 50 of the combustion chamber 12 is possible.

The light-guide ends 44 are shaped or, where applicable, ground such that a central direction of incidence E of the electromagnetic radiation out of the combustion chamber 12, this direction forming an angle bisector of the aperture A, can extend at an angle to the central axis 40 and preferably also at an angle to a longitudinal direction 52 of the passage 30 in a section 54 of the passage 30 which follows the section 46 and extends as far as an opening 56 of the passage 30 which is located so as to be remote from the combustion chamber 12 and from which, for example, the light guide 42 is led out and guided to a diagnosis generating unit 60.

Figure 4:
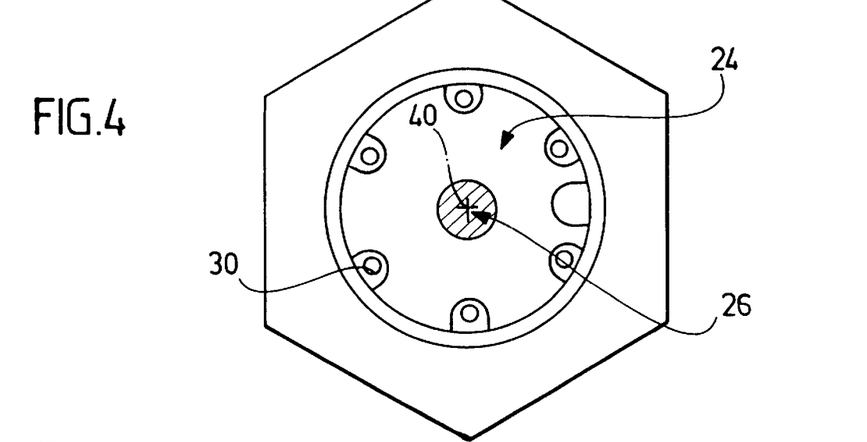
FIG. 4 shows a section along line 4—4 in FIG. 2.

As illustrated in FIG. 4, a plurality of individual passages 30 are preferably provided in the ceramic member 24 around the central axis 40 at essentially constant radial distances and essentially constant angular distances. Light guides 42 are guided through these passages and are each in a position, with their light-guide ends 44 on the side of the combustion chamber, to detect electromagnetic radiation from a spatial segment 50 of the combustion chamber allocated individually to each individual light guide, wherein the entire spatial segments 50 are arranged around the central axis 40 and defined such that they do not overlap one another but preferably supplement one another to from an annular chamber extending around the central axis 40. It is thus possible due to each of the various light guides 42 to detect electromagnetic radiation from another respective spatial segment 50 of the combustion chamber 12 and thus detect the combustion occurring in the combustion chamber 12 with spatial resolution of the resulting electromagnetic radiation.

Figure 5:
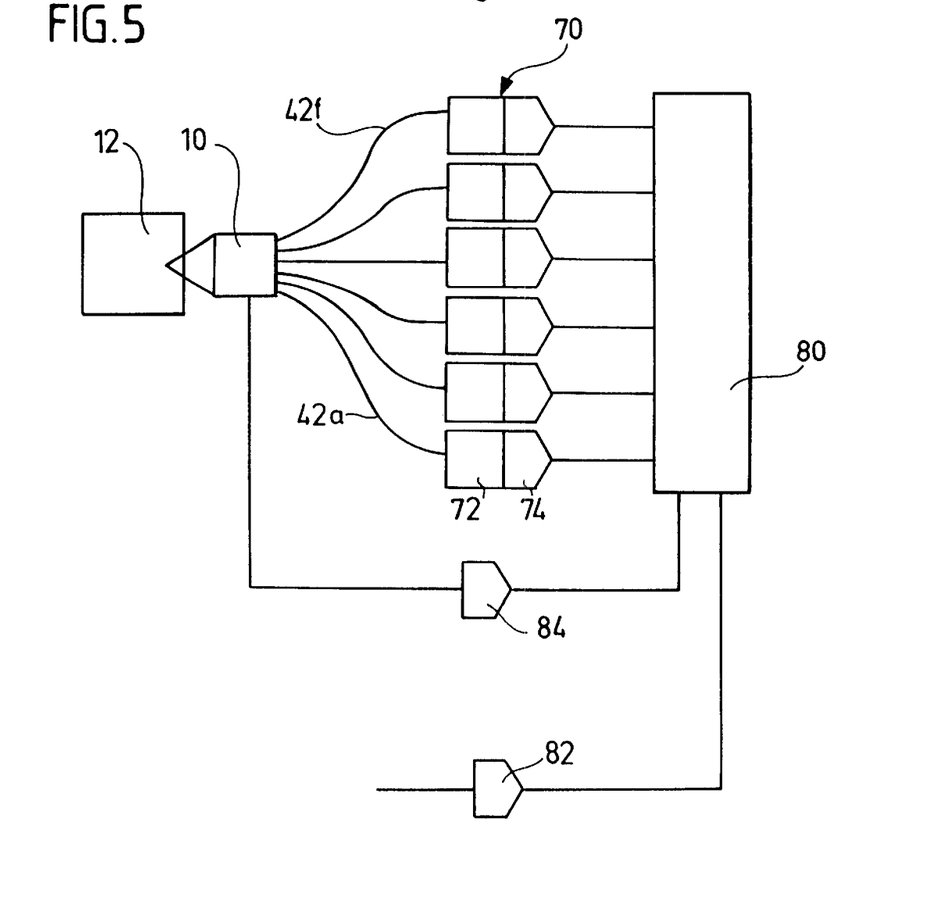
FIG. 5 shows a schematic illustration of the inventive diagnostic system with individual components of the diagnosis evaluation unit.

The diagnosis generating unit 60 is, as illustrated in FIG. 5, designed such that it has for each of the light guides 42a to f a separate detection unit 70 which comprises a spectrally resolving element 72 and an element 74 detecting individual spectral components so that it is possible to detect the quality of the combustion in a spectrally resolved manner via individual spectral lines of the electromagnetic radiation.

Figure 6:
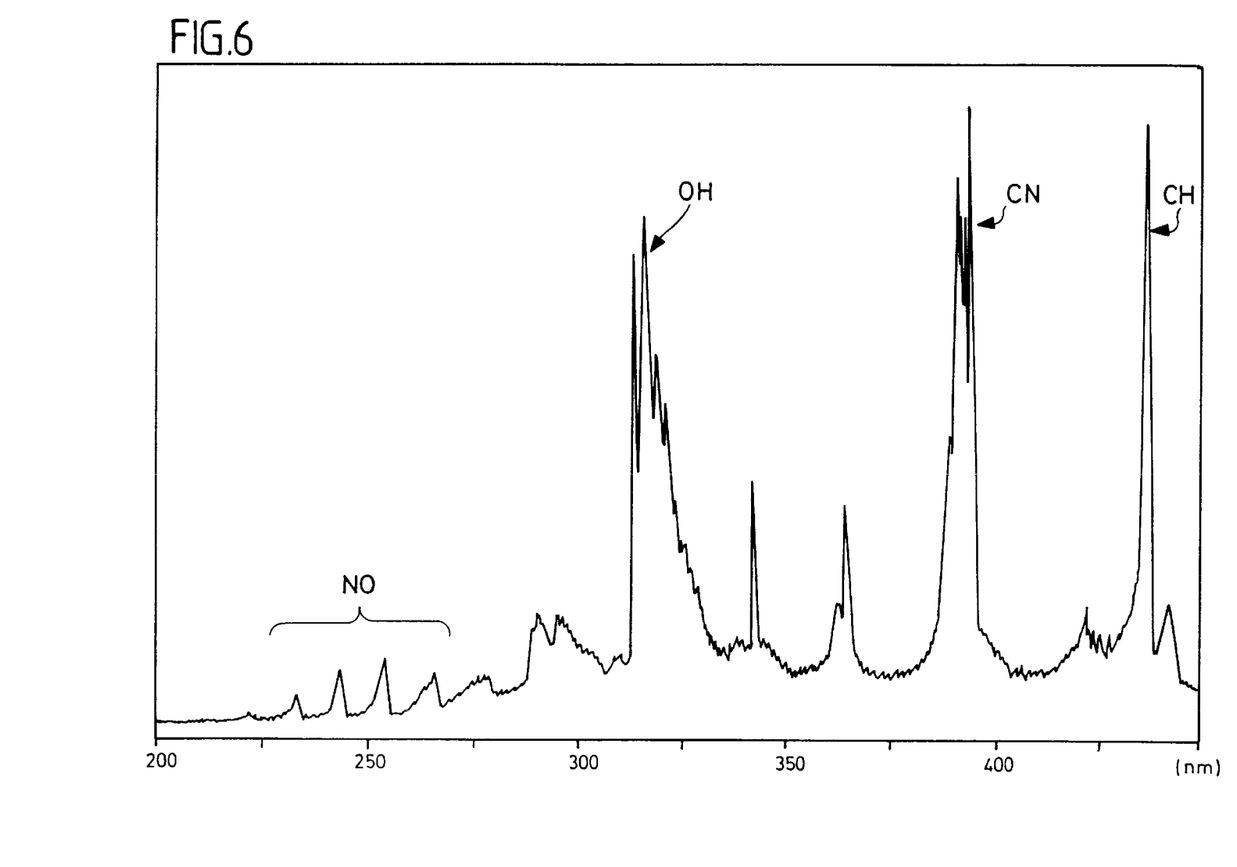
FIG. 6 shows an exemplary illustration of a spectrum of the electromagnetic radiation during poor combustion.
Figure 7:
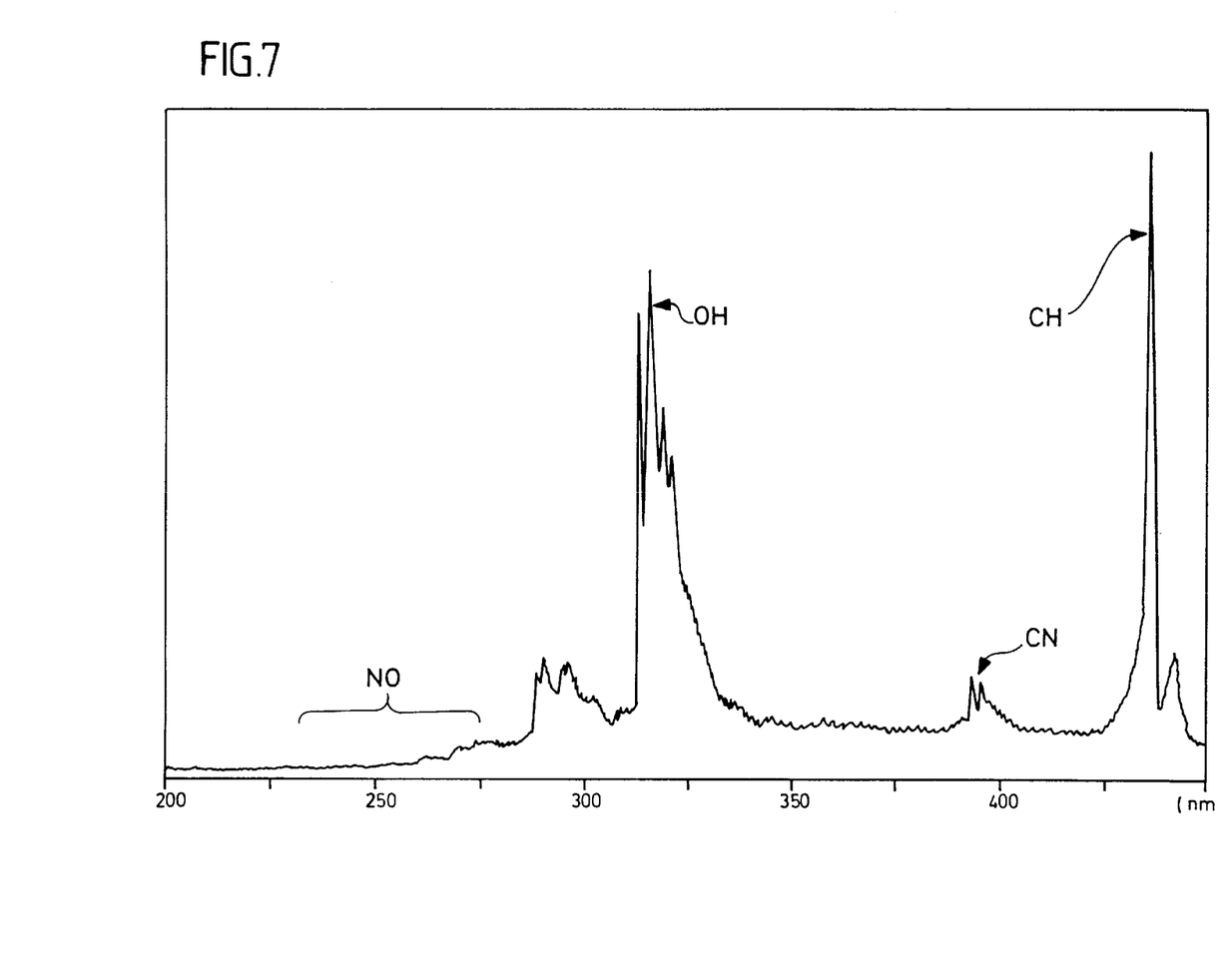
FIG. 7 shows a schematic illustration of the spectrum of the electromagnetic radiation during good combustion.

For example, if a poor combustion is present, as illustrated in FIG. 6, the spectral lines of NO and CN are extremely prominent in comparison with the spectral lines of OH and CH; if, as illustrated in FIG. 7, an essentially ideal combustion is present, the spectral lines of CN and NO are suppressed to a considerable extent in relation to the spectral lines of CH and OH.

It is thus possible to detect the quality of the combustion of the fuel in the individual spatial segments 50a to 50f in a resolved manner. This preferably takes place in an evaluation unit which is designated as a whole as 80 and detects the mechanical state, for example in the case of a piston engine the position of the piston or of the crankshaft, preferably and in addition via a sensor 82, for example a Hall sensor for detecting mechanical states, and the pressure in the combustion chamber via a pressure sensor 84.

The optimum course of combustion can be determined for a given combustion chamber and a predetermined load point of the combustion system from the combustion process resolved spectrally, spatially and with respect to time as a result of optimizing, for example, ignition point and injection process. For example, an optimization to a minimum production of pollutants is possible. It would, however, also be conceivable to bring about an optimization with respect to other criteria, for example, optimum energy conversion etc.

With this procedure for each load point of the corresponding combustion system, for example, the engine, a field of characteristics is obtained for the combustion optimized with regard to the respective criterion. This field of characteristics can then be stored in a corresponding control, for example, engine control electronics and then used for operating the combustion system.

The pressure sensor 84 can likewise be preferably integrated in the diagnostic element, as will be described in detail in the following.

Figure 8:
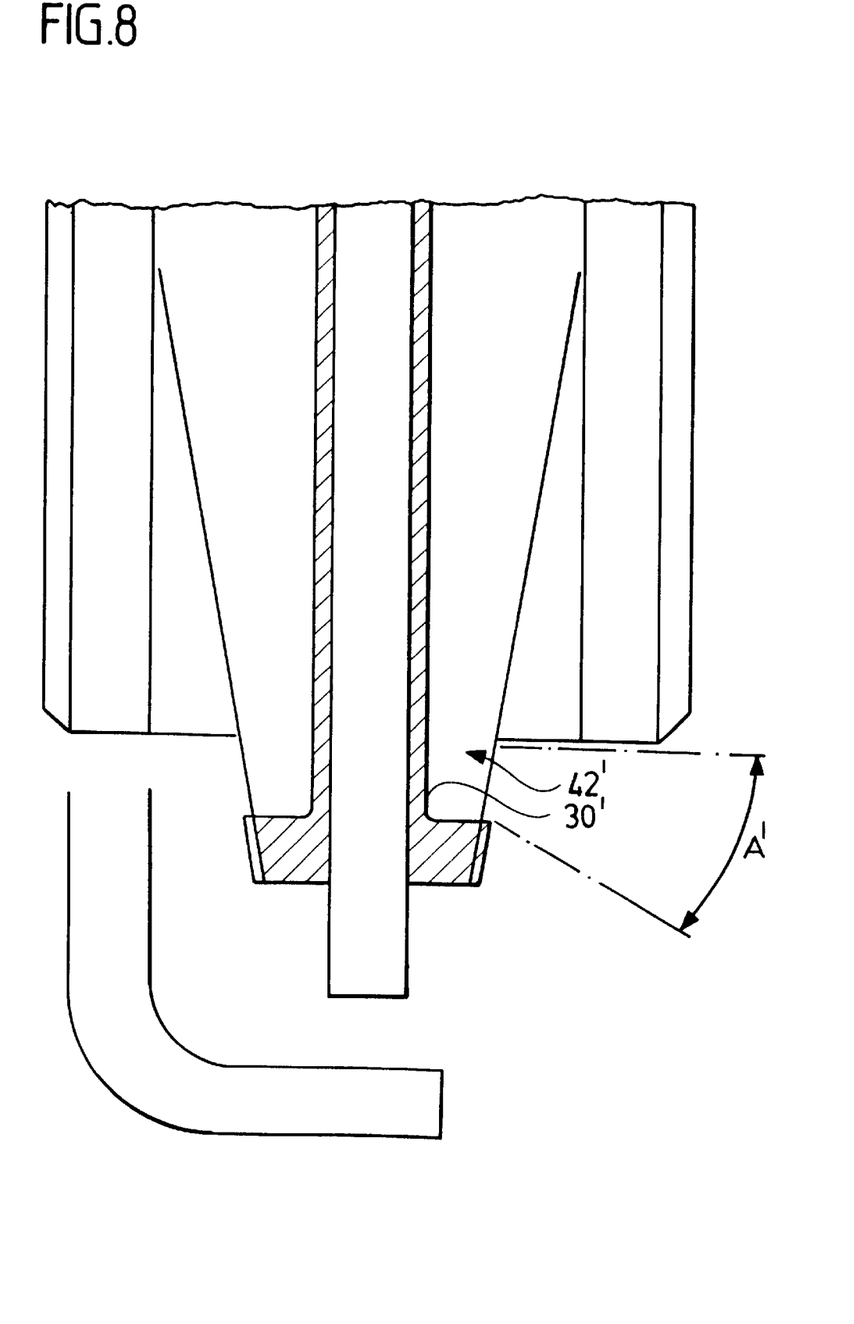
FIG. 8 shows an illustration similar to FIG. 3 of a variation of the first embodiment.

In a variation of the diagnostic element designed as an ignition plug, illustrated in FIG. 8, instead of the passages 30 for the light guides 42 the passages 30' in the ceramic member 24 are enlarged such that plate-like light guides 42', which provide the possibility of selecting the aperture A' to be larger, are used instead of the fiber-like light guides 42.

As for the rest, a coupling to fiber-like light guides likewise occurs in order to guide the electromagnetic radiation to the detection units 70.

In addition to the guidance of the light guides through the passages 30 of the diagnostic element, it is also possible in a further, advantageous embodiment to provide the screw-in member 16 with additional passages and, in addition, with light guides guided through the passages to the combustion chamber.

Furthermore, it is also conceivable to provide the high-voltage electrode 26 with a central passage, through which a light guide is guided which is then in a position, for example, via a bore provided in the earth electrode 22 to detect a spatial segment immediately next to the central axis 40 or one extending around this.

In this respect, it is, for example, possible to also detect the ignition spark via the detection of the spatial segment located close to the central axis 40. This signal obtained from the detected ignition spark can then serve as trigger signal for the detection of the course of the combustion with respect to time, wherein all the detected elements can, for example, be triggered with the trigger signal.

Figure 9:
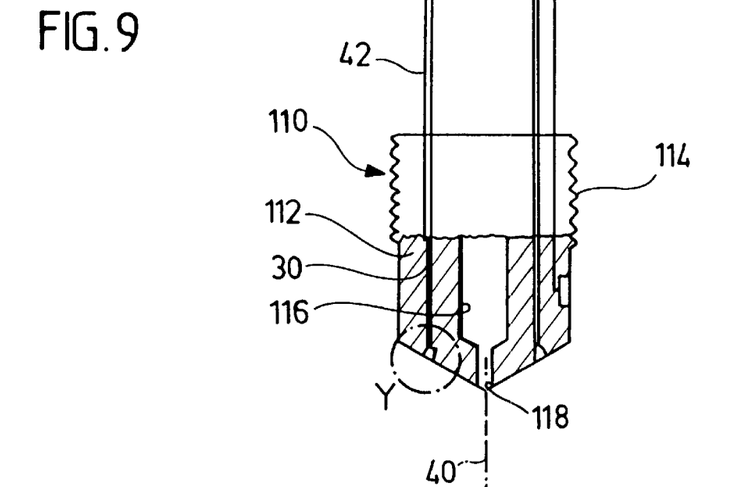
FIG. 9 shows a longitudinal section through a diagnostic element in accordance with a second embodiment.
Figure 10:
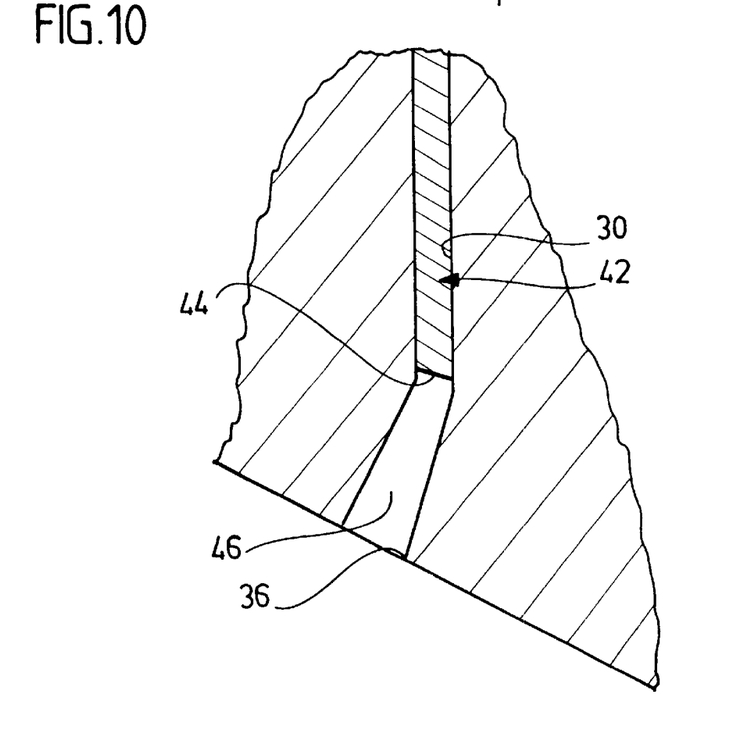
FIG. 10 shows an enlarged detailed illustration of the area Y in FIG. 9.

In a second embodiment of an inventive diagnostic element 110, illustrated in FIGS. 9 and 10, this is no longer a customary ignition plug which is provided with the passages 30 for the fiber-like light guides 42 but an injection nozzle which comprises a nozzle member 112 which is provided with an external thread 114 and has an internal injection channel 116 with an injection nozzle 118 facing the combustion chamber 12.

Furthermore, the nozzle member 112 is penetrated by passages 30, through which the light guides 42 are guided, wherein the light-guide end 44 remains in the passage 30 at a distance from the opening 36 of the passage on the side of the combustion chamber, in the same way as in the first embodiment, and the section 46 of the passage between the light-guide end 44 on the side of the combustion chamber and the opening 36 of the passage on the side of the combustion chamber represents the aperture stop.

Due to the fact that a plurality of passages 30 are provided in the nozzle member 112 around the central axis 40, the possibility of a spatial resolution of the electromagnetic radiation on account of separate reception thereof from different spatial segments is provided in the same way as in the first embodiment.

Figure 11:
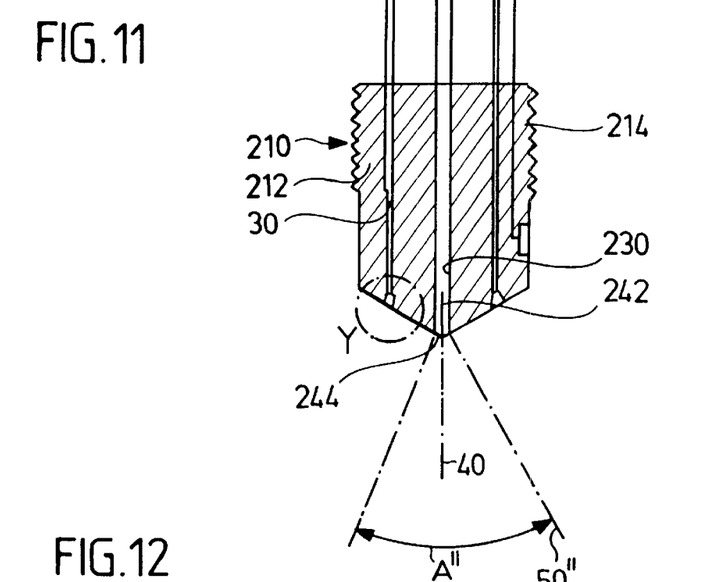
FIG. 11 shows a longitudinal section similar to FIG. 9 through a third embodiment of an inventive diagnostic element and FIG. 12 shows a detailed, enlarged section of the area Y in FIG. 11.
Figure 12:
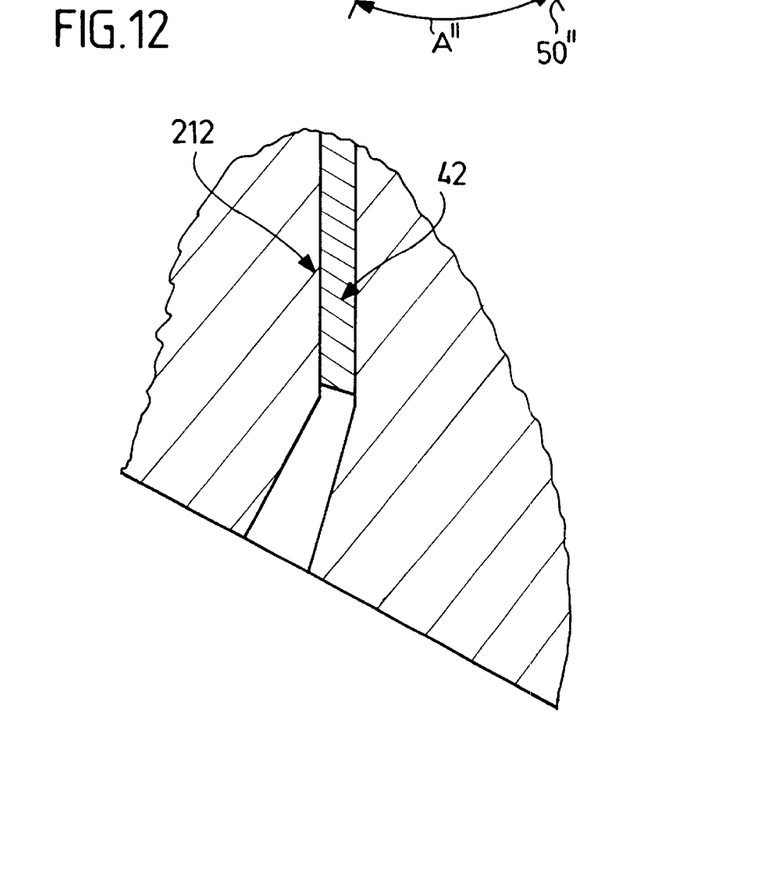

In a third embodiment of an inventive diagnostic element 210, illustrated in FIGS. 11 and 12, a screw-in member 212 is provided which can be screwed with an external thread 214 into a diagnostic bore in the housing of the combustion chamber provided especially for it. The screw-in member 212 is provided in the same way as the nozzle chamber 112 with the passages 30, through which the light guides 42 are guided and, in addition, a central passage 230 is also provided for a central light guide 242, the front light-guide end 244 of which is arranged so as to be coaxial to the central axis 40 and detects a spatial segment 50″ located symmetrical to the central axis 40 with an aperture A″.

A central spatial segment 50″ can thus be detected in a spatially resolved manner with the diagnostic element 210 in addition to the spatial segments 50a to f.

What is claimed is:

1. Combustion diagnosis system for a combustion chamber of a combustion system, comprising:

a diagnostic element insertable into a single bore of a combustion chamber wall and communicating with the combustion chamber;

a plurality of light guides penetrating said diagnostic element for detecting electromagnetic radiation occurring in the combustion chamber; and a plurality of detection units, each detection unit being associated with a corresponding light guide;

wherein:

each light guide guides the electromagnetic radiation from a spatial segment of the combustion chamber associated with said light guide;

said spatial segments of said combustion chamber are arranged around a central axis and expand outward from said central axis;

said spatial segments are different respective segments of the combustion chamber which are arranged so as not to overlap; and each detection unit detects the electromagnetic radiation from said corresponding light guide in spectral resolution.

2. Combustion diagnosis system as defined in claim 1, wherein said central axis represents a central axis of said diagnostic element.

3. Combustion diagnosis system as defined in claim 2, wherein said spatial segments are arranged symmetrically around said central axis.

4. Combustion diagnosis system as defined in claim 2, wherein the sum of all said spatial segments covers a subsection of said combustion chamber extending around said central axis to a considerable proportion.

5. Combustion diagnosis system as defined in claim 1, wherein said light guides are arranged in a passage in a member of said diagnostic element.

6. Combustion diagnosis system as defined in claim 5, wherein one light-guide end of the light guides is located in said passage in front of an opening thereof facing said combustion chamber.

7. Combustion diagnosis system as defined in claim 6, wherein a section of said passage located between said light-guide end and the opening of the passage facing said combustion chamber forms an aperture stop for the electromagnetic radiation entering the light guide.

8. Combustion diagnosis system as defined in claim 7, wherein the cross-section of said section is designed to broaden from said light-guide end as far as said opening of said passage facing said combustion chamber.

9. Combustion diagnosis system as defined in claim 1, wherein the diagnostic element is a functionally necessary element of the combustion system.

10. Combustion diagnosis system as defined in claim 1, wherein said light guides are connected to a diagnosis generating unit.

11. Combustion diagnosis system as defined in claim 1, wherein each of said detection units detects several spectral components of the electromagnetic radiation.

12. Combustion diagnosis system as defined in claim 1, wherein all of said detection units are coupled to a common evaluation unit.

13. Combustion diagnosis system as defined in claim 1, wherein said diagnostic element is provided with a pressure sensor for detecting the pressure in said combustion chamber.

14. Combustion diagnosis system as defined in claim 13, wherein the evaluation unit is coupled to said pressure sensor.

15. Combustion diagnosis system as defined in claim 1, wherein said evaluation unit detects a mechanical state of said combustion system using a separate sensor.

* * * * *